(12) United States Patent
Roodbeen

(10) Patent No.: US 11,964,231 B2
(45) Date of Patent: *Apr. 23, 2024

(54) SYSTEM AND METHOD FOR SEPARATING A GAS MIXTURE

(71) Applicant: Haffmans B.V., Venlo (NL)

(72) Inventor: J. E. Roodbeen, Venlo (NL)

(73) Assignee: HAFFMANS B.V., Venlo (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,287

(22) Filed: Oct. 18, 2022

(65) Prior Publication Data

US 2023/0115430 A1 Apr. 13, 2023

Related U.S. Application Data

(63) Continuation of application No. 16/788,912, filed on Feb. 12, 2020, now Pat. No. 11,471,823.
(Continued)

(51) Int. Cl.
*B01D 53/22* (2006.01)

(52) U.S. Cl.
CPC ......... *B01D 53/226* (2013.01); *B01D 53/227* (2013.01); *B01D 2256/245* (2013.01);
(Continued)

(58) Field of Classification Search
CPC ............... B01D 53/226; B01D 53/227; B01D 2317/022; B01D 2317/025
See application file for complete search history.

(56) References Cited

U.S. PATENT DOCUMENTS

| 1,008,632 A | 11/1911 | Fenlason |
| 3,534,528 A | 10/1970 | James |
| (Continued) | | |

FOREIGN PATENT DOCUMENTS

| CA | 2266567 A1 | 6/2000 |
| EP | 0390992 B1 | 6/1994 |
| (Continued) | | |

OTHER PUBLICATIONS

Examination Report issued for European Patent Application No. 20157030.6 dated May 19, 2022, 4 pages.
(Continued)

*Primary Examiner* — Jason M Greene
(74) *Attorney, Agent, or Firm* — HUSCH BLACKWELL LLP

(57) ABSTRACT

An apparatus and process for separating a gas mixture is disclosed. The apparatus includes a plurality of membrane separation stages comprising a first membrane stage, a second membrane stage, and a third membrane stage. Each of the first, second, and third membrane stages are designed to separate a gas stream provided to them into a permeate stream and a retentate stream. The retentate stream provided from the third membrane stage is configured to be withdrawn as a product, further processed, or discarded. The apparatus further includes a gas transport device with an inlet in communication with the gas mixture and an outlet in communication with the first membrane stage. The controller is in communication with at least one measuring device, and the controller adapts a behavior of the gas transport device in response to a measurement of the at least one measuring device.

20 Claims, 5 Drawing Sheets

Related U.S. Application Data

(60) Provisional application No. 62/804,338, filed on Feb. 12, 2019.

(52) U.S. Cl.
CPC .... *B01D 2257/504* (2013.01); *B01D 2258/05* (2013.01); *B01D 2311/2512* (2022.08); *B01D 2317/025* (2013.01)

(56) References Cited

U.S. PATENT DOCUMENTS

| | | |
|---|---|---|
| 3,713,271 A | 1/1973 | Franz et al. |
| 4,119,417 A | 10/1978 | Heki et al. |
| 4,130,403 A | 12/1978 | Cooley et al. |
| 4,140,499 A | 2/1979 | Ozaki et al. |
| 4,264,338 A | 4/1981 | Null |
| 4,386,944 A | 6/1983 | Kimura |
| 4,435,191 A | 3/1984 | Graham |
| 4,477,420 A | 10/1984 | Bauer et al. |
| 4,518,399 A | 5/1985 | Croskell et al. |
| 4,639,257 A | 1/1987 | Duckett et al. |
| 4,690,695 A | 9/1987 | Doshi |
| 4,857,082 A | 8/1989 | Dimartino, Sr. et al. |
| 4,994,094 A | 2/1991 | Behling et al. |
| 5,089,033 A | 2/1992 | Wijmans |
| 5,102,432 A | 4/1992 | Prasad |
| 5,141,642 A | 8/1992 | Kusuki et al. |
| 5,199,962 A | 4/1993 | Wijmans |
| 5,281,253 A | 1/1994 | Thompson |
| 5,282,969 A | 2/1994 | Xu |
| 5,306,427 A | 4/1994 | Xu |
| 5,378,263 A | 1/1995 | Prasad |
| 5,401,300 A | 3/1995 | Lokhandwala et al. |
| 5,407,466 A | 4/1995 | Lokhandwala et al. |
| 5,407,467 A | 4/1995 | Lokhandwala et al. |
| 5,482,539 A | 1/1996 | Callahan |
| 5,556,449 A | 9/1996 | Baker et al. |
| 5,558,698 A | 9/1996 | Baker et al. |
| 5,632,803 A | 5/1997 | Stoner et al. |
| 5,709,732 A | 1/1998 | Prasad |
| 5,753,011 A | 5/1998 | Sircar et al. |
| 5,762,685 A | 6/1998 | Baker et al. |
| 5,827,351 A | 10/1998 | Prasad et al. |
| 5,837,032 A | 11/1998 | Moll et al. |
| 5,873,928 A | 2/1999 | Callahan |
| 5,919,285 A | 7/1999 | Li et al. |
| 6,035,641 A | 3/2000 | Lokhandwala |
| 6,053,965 A | 4/2000 | Lokhandwala |
| 6,096,114 A | 8/2000 | Li et al. |
| 6,128,919 A | 10/2000 | Daus et al. |
| 6,168,648 B1 | 1/2001 | Ootani et al. |
| 6,168,649 B1 | 1/2001 | Jensvold et al. |
| 6,180,008 B1 | 1/2001 | White |
| 6,221,131 B1 | 4/2001 | Behling et al. |
| 6,254,666 B1 | 7/2001 | Li et al. |
| 6,361,582 B1 | 3/2002 | Pinnau et al. |
| 6,361,583 B1 | 3/2002 | Pinnau et al. |
| 6,425,267 B1 | 7/2002 | Baker et al. |
| 6,428,606 B1 | 8/2002 | Gottschlich et al. |
| 6,565,626 B1 | 5/2003 | Baker et al. |
| 6,572,678 B1 | 6/2003 | Wijmans et al. |
| 6,572,679 B2 | 6/2003 | Baker et al. |
| 6,630,011 B1 | 10/2003 | Baker et al. |
| 6,632,266 B2 | 10/2003 | Thomas et al. |
| 6,648,944 B1 | 11/2003 | Baker et al. |
| 6,709,491 B2 | 3/2004 | Kawakami et al. |
| 6,767,385 B2 | 7/2004 | Brazier |
| 6,830,691 B2 | 12/2004 | Colling et al. |
| 6,921,428 B2 | 7/2005 | Yamamoto et al. |
| 7,537,641 B2 | 5/2009 | Lokhandwala et al. |
| 7,575,624 B2 | 8/2009 | Cartwright et al. |
| 7,604,681 B2 | 10/2009 | Malsam et al. |
| 7,947,117 B2 | 5/2011 | Girdoudiere et al. |
| 7,964,020 B2 | 6/2011 | Baker et al. |
| 8,153,006 B1 | 4/2012 | Fessler et al. |
| 8,192,524 B2 | 6/2012 | Chinn et al. |
| 8,317,900 B2 | 11/2012 | Peinemann et al. |
| 8,366,804 B2 | 2/2013 | Liu et al. |
| 8,388,732 B2 | 3/2013 | Doong et al. |
| 8,419,828 B2 | 4/2013 | Diaz et al. |
| 8,444,749 B2 | 5/2013 | Sanders et al. |
| 8,500,864 B2 | 8/2013 | Gunther |
| 8,568,512 B2 | 10/2013 | Siegel et al. |
| 8,669,083 B2 | 3/2014 | Veit et al. |
| 8,673,056 B2 | 3/2014 | De Bas et al. |
| 8,828,120 B2 | 9/2014 | Szivacz et al. |
| 8,999,038 B2 | 4/2015 | Ungerank et al. |
| 9,309,476 B2 | 4/2016 | Graf |
| 9,314,735 B2 | 4/2016 | Balster et al. |
| 9,433,888 B2 | 9/2016 | Kulkarni |
| 9,713,791 B2 | 7/2017 | Priske et al. |
| 9,770,687 B2 | 9/2017 | Ungerank et al. |
| 9,776,129 B2 | 10/2017 | Heirman |
| 9,969,949 B1 | 5/2018 | Foody et al. |
| 9,988,326 B2 | 6/2018 | Paget et al. |
| 9,993,768 B2 | 6/2018 | W Mustapa et al. |
| 10,086,325 B2 | 10/2018 | Lee et al. |
| 10,471,380 B2 | 11/2019 | Priske |
| 11,471,823 B2 * | 10/2022 | Roodbeen ............ B01D 53/226 |
| 2007/0125537 A1 * | 6/2007 | Lokhandwala ........ B01D 53/22 |
| | | 166/308.4 |
| 2010/0107872 A1 | 5/2010 | Warwick |
| 2010/0317091 A1 | 12/2010 | Veit et al. |
| 2011/0009684 A1 * | 1/2011 | Diaz .................... B01D 53/225 |
| | | 585/818 |
| 2011/0244555 A1 | 10/2011 | Gunther |
| 2012/0097027 A1 | 4/2012 | Gunther |
| 2012/0135491 A1 | 5/2012 | Guenter |
| 2015/0129413 A1 | 5/2015 | Huang et al. |
| 2015/0336046 A1 * | 11/2015 | Ungerank ............ B01D 53/226 |
| | | 96/7 |
| 2016/0228828 A1 | 8/2016 | Balster et al. |
| 2016/0288047 A1 * | 10/2016 | Fukuda ................ B01D 53/226 |
| 2016/0346727 A1 | 12/2016 | Yeo et al. |
| 2017/0283292 A1 * | 10/2017 | Kim .................... B01D 53/226 |
| 2017/0361264 A1 | 12/2017 | Meyer |
| 2017/0368497 A1 | 12/2017 | Priske |
| 2018/0207577 A1 | 7/2018 | Gu et al. |
| 2019/0046922 A1 | 2/2019 | Jensvold et al. |
| 2019/0184332 A1 | 6/2019 | Cnop et al. |
| 2020/0316516 A1 | 10/2020 | Wu et al. |
| 2021/0339189 A1 | 11/2021 | Winkler |

FOREIGN PATENT DOCUMENTS

| | | |
|---|---|---|
| EP | 0490322 B1 | 8/1997 |
| EP | 1324815 A1 | 7/2003 |
| EP | 1360985 A1 | 11/2003 |
| EP | 1434642 A1 | 7/2004 |
| EP | 1515790 A2 | 3/2005 |
| EP | 1754695 A1 | 2/2007 |
| EP | 1953130 A1 | 8/2008 |
| EP | 1287874 B1 | 1/2009 |
| EP | 2017222 A1 | 1/2009 |
| EP | 2296794 A1 | 3/2011 |
| EP | 2335815 A1 | 6/2011 |
| EP | 2440312 A1 | 4/2012 |
| EP | 2471592 A1 | 7/2012 |
| EP | 2588217 A1 | 5/2013 |
| EP | 2296784 B1 | 9/2013 |
| EP | 2666868 A1 | 11/2013 |
| EP | 2735355 A1 | 5/2014 |
| EP | 2797676 A1 | 11/2014 |
| EP | 2919888 A1 | 9/2015 |
| EP | 2974781 A1 | 1/2016 |
| EP | 2996794 A1 | 3/2016 |
| EP | 3027298 A1 | 6/2016 |
| EP | 3032205 A3 | 12/2016 |
| EP | 2104548 B1 | 3/2017 |
| EP | 3240620 A1 | 11/2017 |
| EP | 2206546 B1 | 7/2018 |
| EP | 3338876 B1 | 7/2020 |
| EP | 3463624 B1 | 6/2021 |

(56) References Cited

FOREIGN PATENT DOCUMENTS

| | | | |
|---|---|---|---|
| EP | 3860742 | A1 | 8/2021 |
| EP | 3917649 | A1 | 12/2021 |
| WO | 199611048 | A1 | 4/1996 |
| WO | 0016879 | A1 | 3/2000 |
| WO | 0033949 | A1 | 6/2000 |
| WO | 2005032702 | A1 | 4/2005 |
| WO | 2008079609 | A1 | 7/2008 |
| WO | 2009073029 | A1 | 6/2009 |
| WO | 2012000727 | A1 | 1/2012 |
| WO | 2012095099 | A2 | 7/2012 |
| WO | 2012128648 | A1 | 9/2012 |
| WO | 2013169093 | A1 | 11/2013 |
| WO | 2014075850 | A1 | 5/2014 |
| WO | 2015036709 | A1 | 3/2015 |
| WO | 2017206069 | A1 | 12/2017 |

OTHER PUBLICATIONS

"Process analytics support higher yields in biogas plants," Siemans, Aug. 2010, 12 pages.
Allegue et al., "Biogas and bio-syngas upgrading," Danish Technological Institute, Dec. 2012, 97 pages.
Langerak et al., "Biogas upgrading: Membrane separation takes over," DMT Environmental Technological, Nov. 21, 2015, 10 pages.
Extended European Search Report, European Application No. 20157030. 6, dated Jul. 20, 2020, 7 pages.
Basu et al., "Membrane-based technologies for biogas separations", Chemical Society Reviews, 39, Oct. 6, 2009, 6 pp. 750-768.

* cited by examiner

SYSTEM AND METHOD FOR SEPARATING A GAS MIXTURE

CROSS-REFERENCE TO RELATED APPLICATIONS

The instant application claims priority to U.S. Provisional Patent Application No. 62/804,338, filed on Feb. 12, 2019, and co-pending U.S. patent application Ser. No. 16/788,912, filed on Feb. 12, 2020. The aforementioned patent applications are incorporated by reference in their entirety herein.

BACKGROUND

Polymeric gas separation membranes are well known and commonly used in industry to purify, upgrade, and/or remove a desired component from gas mixtures. Common industrial uses for gas separation membranes include the recovery of hydrogen from gas mixtures (e.g., ammonia or oil refinery process streams), the recovery of methane from gas mixtures (e.g., natural gas or biogas), the production of oxygen-enriched air, and/or the removal of impurities from gas streams (e.g., removal of water vapor, volatile organic compounds, and $H_2S$).

Recently, there has been an increased interest in separation systems that separate methane from biogas or natural gas streams. Methane, especially biomethane, is a desirable product as it can be used in a variety of commercial applications, such as a source of energy for heating, for the production of chemicals, or for use as a fuel, among others. However, efficiently separating methane from carbon dioxide is a non-trivial task owing to the low selectivity of polymeric membrane materials to these gases. In order to counteract the low single-stage selectivity, commercial systems typically utilize three or more membrane stages operating at high pressures to achieve the desired purity.

Gas separation at an industrial scale is challenging. Unlike laboratory conditions that are typically performed using pure gas samples at modest temperatures and pressures, industrial conditions include exposing the membranes to multi-component gas streams having contaminated liquid and/or solid impurities, while operating at elevated temperatures and pressure. Often times, the gas source provides the gas mixture to the separation system irregularly, for example. The gas mixture typically fluctuates both in composition and flow rate over time, making it difficult to control the gas separation system to reliably and consistently produce a desired purity of the product gas stream.

Currently, there remains a need for improvements to existing commercial gas separation processes to develop more cost effective and energy efficient systems that exhibit superior process control, especially for processes directed to separating methane from biogas and natural gas streams.

SUMMARY OF THE DISCLOSURE

The present disclosure addresses the aforementioned drawbacks by providing a process for separating a gas mixture using a multi-stage membrane separation system having reduced operational costs and improved separation efficiency over conventional systems.

Some embodiments of the disclosure provide an apparatus for separating a gas mixture having two or more components. In particular, the apparatus includes a plurality of membrane separation stages including a first membrane stage, a second membrane stage, and a third membrane stage. The first membrane stage is designed to separate the gas mixture into a first retentate stream and a first permeate stream, the second membrane stage is designed to separate the first permeate stream into a second retentate stream and a second permeate stream, and the third separation stage is designed to separate the second retentate stream into a third retentate stream and a third permeate stream. The third retentate stream is configured to be withdrawn as a product, further processed, or discarded. The apparatus further comprises a first gas transport device with a first inlet in fluid communication with the gas mixture and a first outlet in fluid communication with the first membrane stage. A controller is in communication with at least one measuring device and the first gas transport device. The at least one measuring device is designed to measure at least one parameter of the gas mixture, the first permeate stream, the second retentate stream, and/or the third retentate stream, and the controller adapts a behavior of the first gas transport device in response to a change in the at least one parameter of the gas mixture, the first permeate stream, the second retentate stream, and/or the third retentate stream, as measured by the at least one measuring device.

In some embodiments, the gas mixture may comprise biogas.

In further embodiments, the at least one measuring device measures at least one parameter associated with the third retentate stream.

In some embodiments, the at least one measuring device is adapted to measure at least one of a pressure, a temperature, a flow rate, a composition, a viscosity, a humidity, a moisture content, or a density of the first permeate stream, the second retentate stream, and/or the third retentate stream.

In further embodiments, the controller includes programming to adjust at least one process parameter of the apparatus in response to measured values obtained from the at least one measuring device in order to maintain a desired set-point in the third retentate stream. In yet further embodiments, the desired set-point is selected from the group consisting of a desired pressure, a desired component composition, a desired flowrate, and combinations thereof.

In some embodiments, the controller is designed to adjust a speed of rotation of the first gas transport device in response to a change in one or more parameters measured by the at least one measuring device.

In further embodiments, the apparatus also comprises a continuing stream that places the first retentate stream in fluid communication with the second retentate stream. The apparatus further includes a second gas transport device with a second inlet in fluid communication with the first retentate stream and a second outlet in communication with the continuing stream. The second gas transport device is in communication with the controller, and the controller adapts the behavior of the second gas transport device in response to the measurement of the at least one parameter by the at least one measuring device.

In some embodiments, an apparatus for separating a gas mixture having at least two components is disclosed. In particular, the apparatus comprises a first membrane separation stage adapted to receive and separate the gas mixture into a first stream and a second stream, the first membrane separation stage comprising a first plurality of membranes having a first total membrane surface area. The apparatus also includes a second membrane separation stage adapted to receive the first stream from the first membrane separation stage, the second membrane separation stage comprising a second plurality of membranes having a second total membrane surface area. A first set of one or more interior control devices coupled to the first membrane separation stage and a second set of one or more interior control devices coupled to the second membrane separation stage is also provided. A controller is in electrical communication with the first membrane separation stage and the second membrane separation stage, and the controller is designed to adjust the first and second sets of the one or more interior control devices.

In further embodiments, the second total membrane surface area is greater than the first total membrane surface area.

In some embodiments, the controller is designed to alter an operational status of one or more membranes of the first and second plurality of membranes via the first and second sets of the one or more interior control devices.

In other embodiments, altering the operational status of the one or more membranes includes allowing gas to flow through at least one of the one or more membranes and/or preventing gas flow through at least one of the one or more membranes. In yet other embodiments, altering the operational status of the one or more membranes comprises turning at least one membrane of the one or more membranes on and/or off.

In further embodiments, the controller changes the operational status of the one or more membranes of the first and second plurality of membranes in response to a change in at least one measured value provided to the controller by at least one measurement device.

In some embodiments, the apparatus further comprises a third membrane separation stage adapted to receive the second stream from the first membrane separation stage, the third membrane separation stage comprising a third plurality of membranes having a third total membrane surface area. The controller is in electrical communication with the third membrane separation stage and is designed to change an operational status of one or more membranes of the third plurality of membranes using one or more interior control devices coupled to the third membrane separation stage.

In further embodiments, the first total membrane surface area and the third total membrane surface area are about equal.

In some embodiments, the apparatus further includes a third membrane separation stage having a third total membrane area. A ratio of the first total membrane surface area, the second total membrane surface area, and the third total membrane surface area is at least about 1:2:1. In yet further embodiments of the invention, the ratio of the first total membrane surface area, the second total membrane surface area, and the third total membrane surface area is at least about 1:4:1.

In further embodiments, the first stream is a permeate stream and the second stream is a retentate stream.

In some embodiments, a ratio of the first total membrane surface area and the second total membrane surface area is at least 1:2. In yet further embodiments, the ratio of the first total membrane surface area and the second total membrane surface area is at least 1:4.

In further embodiments, an apparatus for separating a gas mixture having at least two components is disclosed. In particular, the apparatus comprises a first membrane stage in fluid communication with a gas source comprising a reservoir of the gas mixture, wherein the first membrane stage separates the gas mixture into a first retentate stream and a first permeate stream; a second membrane stage in fluid communication with the first permeate stream, wherein the first membrane stage separates the first permeate stream into a second retentate stream and a second permeate stream; a continuing stream that places the second retentate stream in fluid communication with the continuing stream to form a mixed retentate stream; and a third membrane stage designed to separate the mixed retentate stream into a third permeate stream and a third retentate stream.

In some embodiments, the apparatus further comprises a pretreatment unit positioned between the reservoir and the first membrane stage, the pretreatment unit designed to remove one or more contaminants from the gas mixture.

In further embodiments, the apparatus includes a controller in communication with at least one measuring device, the controller adapted to execute a stored program to adjust a speed of rotation of the first gas transport device to obtain a desired pressure set-point in the continuing stream. In yet further embodiments, the speed of rotation of the first gas transport device is adjusted in response to a change in one or more process parameters measured by the at least one measuring device.

In some embodiments, a measuring device of the at least one measuring device is in communication with the third retentate stream.

In some embodiments, the apparatus includes a controller programmed to acquire at least one process parameter associated with the second retentate stream or the continuing stream. In yet further embodiments, the controller will adjust the first gas transport device to maintain a desired set-point in the continuing stream.

In further embodiments, the desired set-point includes at least one of a desired pressure, a desired component composition, and a desired flowrate.

These and other advantages and features of the present invention will become more apparent from the following detailed description of the preferred embodiments of the present invention when viewed in conjunction with the accompanying drawings.

DETAILED DESCRIPTION

Figure 1:
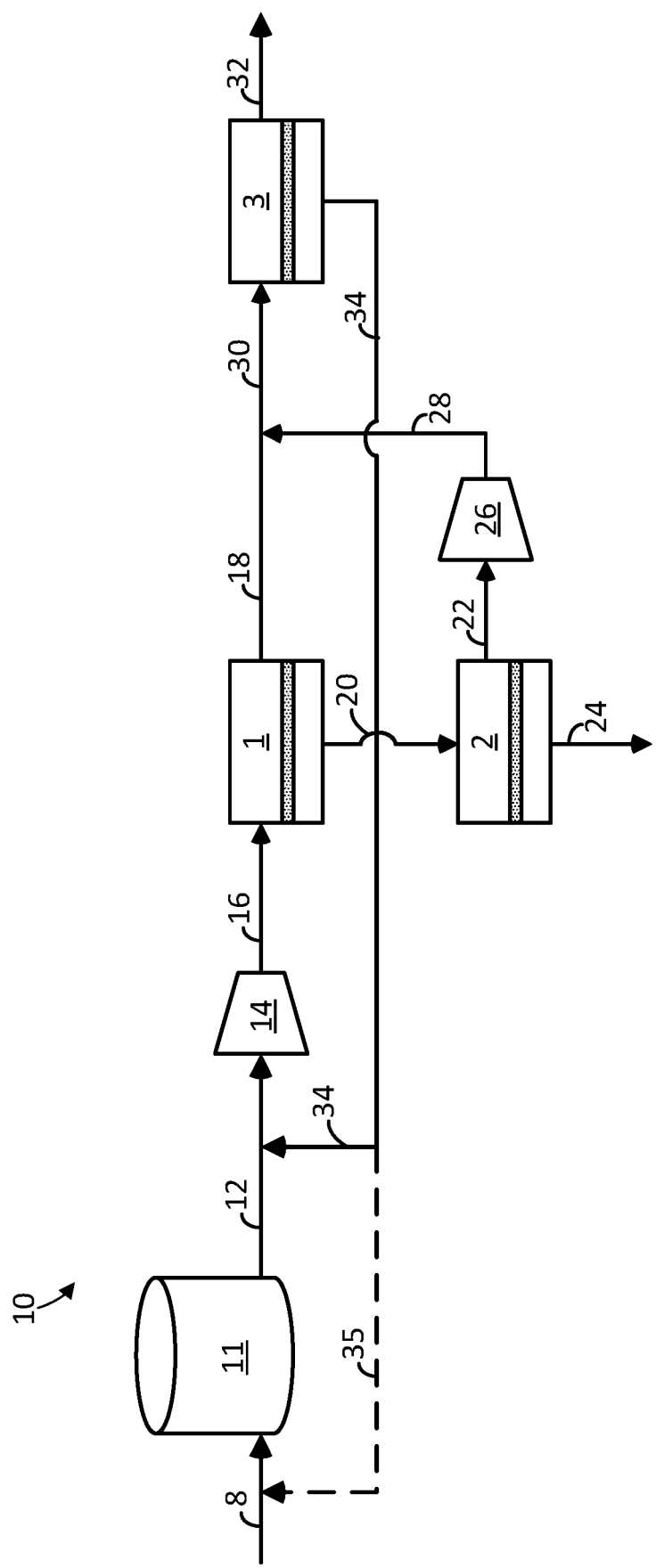
FIG. 1 is a block diagram of an example apparatus for separating a gas mixture in accordance with embodiments of the present disclosure.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the disclosure. Various modifications to the illustrated embodiments will be readily apparent to those skilled in the art, and the generic principles herein can be applied to other embodiments and applications without departing from embodiments of the disclosure. Thus, embodiments of the disclosure are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the disclosure. Skilled artisans will recognize the examples provided herein have many useful alternatives and fall within the scope of embodiments of the disclosure.

Referring now to FIG. 1, an apparatus 10 for separating a gas mixture is shown. In some embodiments, the apparatus 10 includes at least a first membrane separation stage 1, a second membrane stage 2, and a third membrane stage 3. The first membrane separation stage 1 is provided in fluid communication with a gas source 11 comprising a reservoir of the gas mixture. In some embodiments, the gas source 11 may include biogas comprising a variety of components (e.g., methane, carbon dioxide, etc.). The biogas may be produced from sources such as agricultural waste, manure, municipal waste, plant material, sewage, green waste, food waste, anaerobic digester, or combinations thereof, and transferred to the apparatus 10 for separation.

In some embodiments, the apparatus 10 includes a first gas transport device 14 having a suction side connected to an inlet gas line 12 and a discharge side connected to a feed gas line 16. The feed gas line 16 places the first gas transport device 14 in fluid communication with the first membrane stage 1, and the inlet gas line 12 places the first gas transport device 14 in fluid communication with the gas source 11. In general, the gas transport device 14 may be provided as a mechanical device that adjusts (e.g., increases) the pressure of the gas mixture and may comprise a compressor, a blower or the like. In some embodiments, the first gas transport device 14 is configured to feed the gas mixture to the first separation stage 1 at a pressure that ranges between 1.5 bar (150 kPa) to 100 bar (10000 kPa), or more. In other embodiments, the first pressure may range between 5 bar (500 kPa) to 40 bar (4000 kPa), or 5 bar (500 kPa) to 35 bar (3500 kPa), or 5 bar (500 kPa) to 25 bar (2500 kPa). In other embodiments, the first pressure may range between about 1.5 bar (150 kPa) to about 100 bar (10000 kPa), or about 5 bar (500 kPa) to about 40 bar (4000 kPa), or about 5 bar (500 kPa) to about 35 bar (3500 kPa), or about 5 bar (500 kPa) to about 25 bar (2500 kPa).

The first membrane separation stage 1 includes one or more gas separation membranes configured to separate the gas mixture into a first retentate stream 18 and a first permeate stream 20. The first permeate stream 20 includes gas components that pass through the gas separation membrane, while the first retentate stream 18 includes gas components retained by the gas separation membrane. In some embodiments, the gas separation membranes comprise a polymeric membrane. In some embodiments, suitable gas separation materials for use in the first membrane separation stage 1 include those that are selective for carbon dioxide over methane. A measure of the ability of a membrane to separate two gases is the selectivity, $\alpha$, defined as the ratio of the gas permeabilities, P1/P2. Selectivity can also be expressed as:

$$\alpha_{12} = \frac{P_1}{P_2} = \left[\frac{D_1}{D_2}\right]\left[\frac{k_1}{k_2}\right]$$

where D is the diffusion coefficient of the gas in the membrane [cm2/s], which is a measure of the gas mobility, and k is the Henry's law sorption coefficient, which links the concentration of the gas in the membrane material to the pressure in the adjacent gas [$cm^3$ (STP)/$cm^3$·cmHg]. The ratio D1/D2 is the ratio of the diffusion coefficients of the two gases and can be viewed as the mobility selectivity, reflecting the different sizes of the two molecules. The ratio $k_1/k_2$ is the ratio of the Henry's law sorption coefficients of the two gases and can be viewed as the solubility selectivity, reflecting the relative condensabilities of the two gases. Depending on the nature of the polymer, either the diffusion or the sorption component of the permeability may dominate.

In some embodiments, the gas separation membrane of the first membrane separation stage 1 comprises a selectivity of $CO_2/CH_4$ that is greater than 1. In some embodiments the gas separation membrane of first membrane separation stage 1 comprises a selectivity of $CO_2/CH_4$ that is between 1 to 200. In some non-limiting examples, the first membrane separation stage 1 comprises a selectivity of $CO_2/CH_4$ that ranges between 3 to 85, or 10 to 80, or 20 to 70, or 30 to 60, or 45 to 55. In some non-limiting examples, the first membrane separation stage 1 comprises a selectivity of $CO_2/CH_4$ that ranges between about 1 to about 200, or about 3 to about 85, or about 10 to about 80, or about 20 to about 70, or about 30 to about 60, or about 45 to about 55.

In some embodiments, the gas separation membrane of the first membrane separation stage 1 comprises a selectivity of $CO_2/CH_4$ that is at least 5, at least 10, at least 15, at least 20, at least 25, at least 30, at least 35, at least 40, at least 45, at least 50, at least 55, at least 60, at least 65, at least 70, at least 80, at least 85, at least 90, at least 95, at least 100, at least 110, at least 120, at least 130, at least 140, at least 150, at least 160, at least 170, at least 180, at least 190, or at least 200. In some embodiments, the gas separation membrane of the first membrane separation stage 1 comprises a selectivity of $CO_2/CH_4$ that is at least about 5, at least about 10, at least about 15, at least about 20, at least about 25, at least about 30, at least about 35, at least about 40, at least about 45, at least about 50, at least about 55, at least about 60, at least about 65, at least about 70, at least about 80, at least about 85, at least about 90, at least about 95, at least about 100, at least about 110, at least about 120, at least about 130, at least about 140, at least about 150, at least about 160, at least about 170, at least about 180, at least about 190, or at least about 200.

Referring back to FIG. 1, the first permeate stream 20 may be connected to a feed side of the second membrane separation stage 2. The second membrane separation stage 2 includes one or more gas separation membranes that separates the first permeate stream 20 into a second retentate stream 22 and a second permeate stream 24. The second permeate stream 24 may be removed as a product, further processed, or discarded. The second retentate stream 22 is connected to a suction side of an optional second gas transport device 26 that is configured to adjust (e.g., increase) the pressure of the second retentate stream 22. The optional second gas transport device 26 includes a discharge side that dispenses the gas components in the second retentate stream 22 into a continuing stream 28, which places the optional second gas transport device 26 in fluid communication with the first retentate stream 18. During operation, the second retentate stream 22 is mixed with the first retentate 18 through continuing stream 28 to form a mixed gas stream 30.

The optional second gas transport device 26 may comprise a mechanical device that increases the pressure of the second retentate stream 22 and may comprise, for example, a compressor or a blower. In some embodiments, the optional second gas transport device 26 is configured to compress the second retentate stream 22 to a second pressure, which may be the same, or substantially the same, as the pressure of the first retentate stream 18. In an alternative arrangement, the optional second gas transport device 26 may be configured in the first permeate stream 20, and may be configured to compress the first permeate stream 20 such that the second pressure of the continuing stream 28 is the same, or substantially the same, as the pressure of the first retentate stream 18.

In some embodiments, the first gas transport device 14 is designed to have a larger power output than the optional second gas transport device 26. For example, the first gas transport device 14 and the optional second gas transport device 26 may be sized such that the power requirement (actual or theoretical) of the first gas transport device 14 to the optional second gas transport device 26 can range from at least 200:1 to at least 10:1, or from at least about 200:1 to at least about 10:1. In some embodiments, the power requirement of the first gas transport device 14 to the optional second gas transport device 26 is at least 10:1, at least 15:1, at least 20:1, at least 25:1, at least 30:1, at least 35:1, at least 40:1, at least 45:1, at least 50:1, at least 55:1, at least 60:1, at least 65:1, at least 70:1, at least 75:1, at least 80:1, at least 90:1, at least 95:1, or 100:1. In some embodiments, the power requirement of the first gas transport device 14 to the optional second gas transport device 26 is at least about 10:1, at least about 15:1, at least about 20:1, at least about 25:1, at least about 30:1, at least about 35:1, at least about 40:1, at least about 45:1, at least about 50:1, at least about 55:1, at least about 60:1, at least about 65:1, at least about 70:1, at least about 75:1, at least about 80:1, at least about 90:1, at least about 95:1, or about 100:1.

In some non-limiting examples, the gas mixture comprises biogas and, during operation, the methane content in the mixed gas stream 30 is at least 1.1 times greater than the methane content in the feed gas line 16, or at least about 1.1 times greater than the methane content in the feed gas line 16. In some embodiments, the methane content in the mixed gas stream 30 is at least 1.2 times greater, at least 1.3 times greater, at least 1.4 times greater, at least 1.5 times greater, at least 1.6 times greater, at least 1.7 times greater, at least 1.8 times greater, at least 1.9 times greater, or at least 2 times greater than the methane content in the feed gas line 16. In some embodiments, the methane content in the mixed gas stream 30 is at least about 1.2 times greater, at least about 1.3 times greater, at least about 1.4 times greater, at least about 1.5 times greater, at least about 1.6 times greater, at least about 1.7 times greater, at least about 1.8 times greater, at least about 1.9 times greater, or at least about 2 times greater than the methane content in the feed gas line 16.

In some embodiments, the gas separation membrane of the second membrane separation stage 2 comprises a polymeric membrane. In some embodiments, the gas separation membrane of the second membrane separation stage 2 may comprise a selectivity that is the same or different than the first membrane separation stage 1. In some embodiments, the gas separation membrane of the second membrane separation stage 2 comprises a selectivity of $CO_2/CH_4$ that is greater than 1. In some embodiments the gas separation membrane of second membrane separation stage 2 comprises a selectivity of $CO_2/CH_4$ that is 1 to 200, or about 1 to about 200. In some non-limiting examples, the second membrane separation stage 2 comprises a selectivity of $CO_2/CH_4$ that ranges between 3 to 85, or 10 to 80, or 20 to 70, or 30 to 60, or 45 to 55. In some non-limiting examples, the second membrane separation stage 2 comprises a selectivity of $CO_2/CH_4$ that ranges between about 3 to about 85, or about 10 to about 80, or about 20 to about 70, or about 30 to about 60, or about 45 to about 55.

In some embodiments, the gas separation membrane of the second membrane separation stage 2 comprises a selectivity of $CO_2/CH_4$ that is at least 5, at least 10, at least 15, at least 20, at least 25, at least 30, at least 35, at least 40, at least 45, at least 50, at least 55, at least 60, at least 65, at least 70, at least 80, at least 85, at least 90, at least 95, at least 100, at least 110, at least 120, at least 130, at least 140, at least 150, at least 160, at least 170, at least 180, at least 190, or at least 200. In some embodiments, the gas separation membrane of the second membrane separation stage 2 comprises a selectivity of $CO_2/CH_4$ that is at least about 5, at least about 10, at least about 15, at least about 20, at least about 25, at least about 30, at least about 35, at least about 40, at least about 45, at least about 50, at least about 55, at least about 60, at least about 65, at least about 70, at least about 80, at least about 85, at least about 90, at least about 95, at least about 100, at least about 110, at least about 120, at least about 130, at least about 140, at least about 150, at least about 160, at least about 170, at least about 180, at least about 190, or at least about 200.

Referring back to FIG. 1, the mixed gas stream 30 is connected to a feed side of the third membrane separation stage 3. The third membrane separation stage 3 includes a gas separation membrane that separates the mixed gas stream 30 into a third retentate stream 32 and a third permeate stream 34. The third retentate stream 32 may be withdrawn as a product, further processed, or discarded. In some embodiments, the third permeate stream 34 is recycled back to the inlet gas line 12. Alternatively, or additionally, the third permeate stream 34 may be recycled via a recycle line 35 (optional) back to the gas source 11, for example, to a feed inlet 8 configured upstream of the gas source 11. Alternatively, the third permeate stream 34 may be further processed, or discarded.

In some embodiments, the gas separation membrane of the third membrane separation stage 3 comprises a polymeric membrane. In some embodiments, the gas separation membrane of the third membrane separation stage 3 may comprise a selectivity that is the same or different than the first membrane separation stage 1 and/or the second membrane separation stage 2. In some embodiments, the gas separation membrane of the second membrane separation stage 2 comprises a selectivity of $CO_2/CH_4$ that is greater than 1, or greater than about 1. In some embodiments the gas separation membrane of third membrane separation stage 3 comprises a selectivity of $CO_2/CH_4$ that is 1 to 200, or about 1 to about 200. In some non-limiting examples, the third membrane separation stage 2 comprises a selectivity of $CO_2/CH_4$ that ranges between 3 to 85, or 10 to 80, or 20 to 70, or 30 to 60, or 45 to 55. In some non-limiting examples, the third membrane separation stage 2 comprises a selectivity of $CO_2/CH_4$ that ranges between about 3 to about 85, or about 10 to about 80, or about 20 to about 70, or about 30 to about 60, or about 45 to about 55.

In some embodiments, the gas separation membrane of the third membrane separation stage 3 comprises a selectivity of $CO_2/CH_4$ that is at least 5, at least 10, at least 15, at least 20, at least 25, at least 30, at least 35, at least 40, at least 45, at least 50, at least 55, at least 60, at least 65, at least 70, at least 80, at least 85, at least 90, at least 95, at least 100, at least 110, at least 120, at least 130, at least 140, at least 150, at least 160, at least 170, at least 180, at least 190, or at least 200. In some embodiments, the gas separation membrane of the third membrane separation stage 3 comprises a selectivity of $CO_2/CH_4$ that is at least about 5, at least about 10, at least about 15, at least about 20, at least about 25, at least about 30, at least about 35, at least about 40, at least about 45, at least about 50, at least about 55, at least about 60, at least about 65, at least about 70, at least about 80, at least about 85, at least about 90, at least about 95, at least about 100, at least about 110, at least about 120, at least about 130, at least about 140, at least about 150, at least about 160, at least about 170, at least about 180, at least about 190, or at least about 200.

In some embodiments, the first membrane separation stage 1, the second membrane separation stage 2, and/or the third membrane separation stage 3 may include one or more vacuum pumps arranged downstream of the respective membrane separation stage to assist in producing a pressure differential across the gas separation membrane. In some embodiments, the second membrane separation stage 2 and the third membrane separation stage 3 may include one or more vacuum pumps arranged downstream of the respective membrane separation stage to assist in producing a pressure differential across the gas separation membrane. Additionally, or alternatively, the first membrane separation stage 1, the second membrane separation stage 2, and the third membrane separation stage 3 may optionally include a sweep gas flowing along the permeate side of each respective stage to assist the separation.

In some embodiments, a pretreatment unit (not shown in FIG. 1) is configured in the inlet gas line 12 and may be optionally used to remove contaminants from the gas mixture. For example, the pretreatment unit may be configured to perform filtration (e.g., by activated carbon), adsorption, absorption, or condensation to remove one or more contaminants from the gas mixture including, but not limited to siloxanes, volatile organic compounds, $H_2S$, water vapor, and combinations thereof.

The fluid communication within the apparatus 10 disclosed in FIG. 1 offers several advantages over conventional system. For example, one advantage of recycling the second retentate stream 22 to the first retentate stream 18 is that it allows for a reduction in the total amount of gas that is recycled back the first gas transport device 14, as opposed to recycling the second retentate stream 22 back to the inlet gas line 12. This allows for the first gas transport device 14 to be smaller, thereby reducing initial investment costs, lowering operation costs, and maximizing the total system efficiency to allow for a reduction in total membrane area as compared to conventional systems. The apparatus 10 additionally offers improved process control, as will be described.

Figure 2:
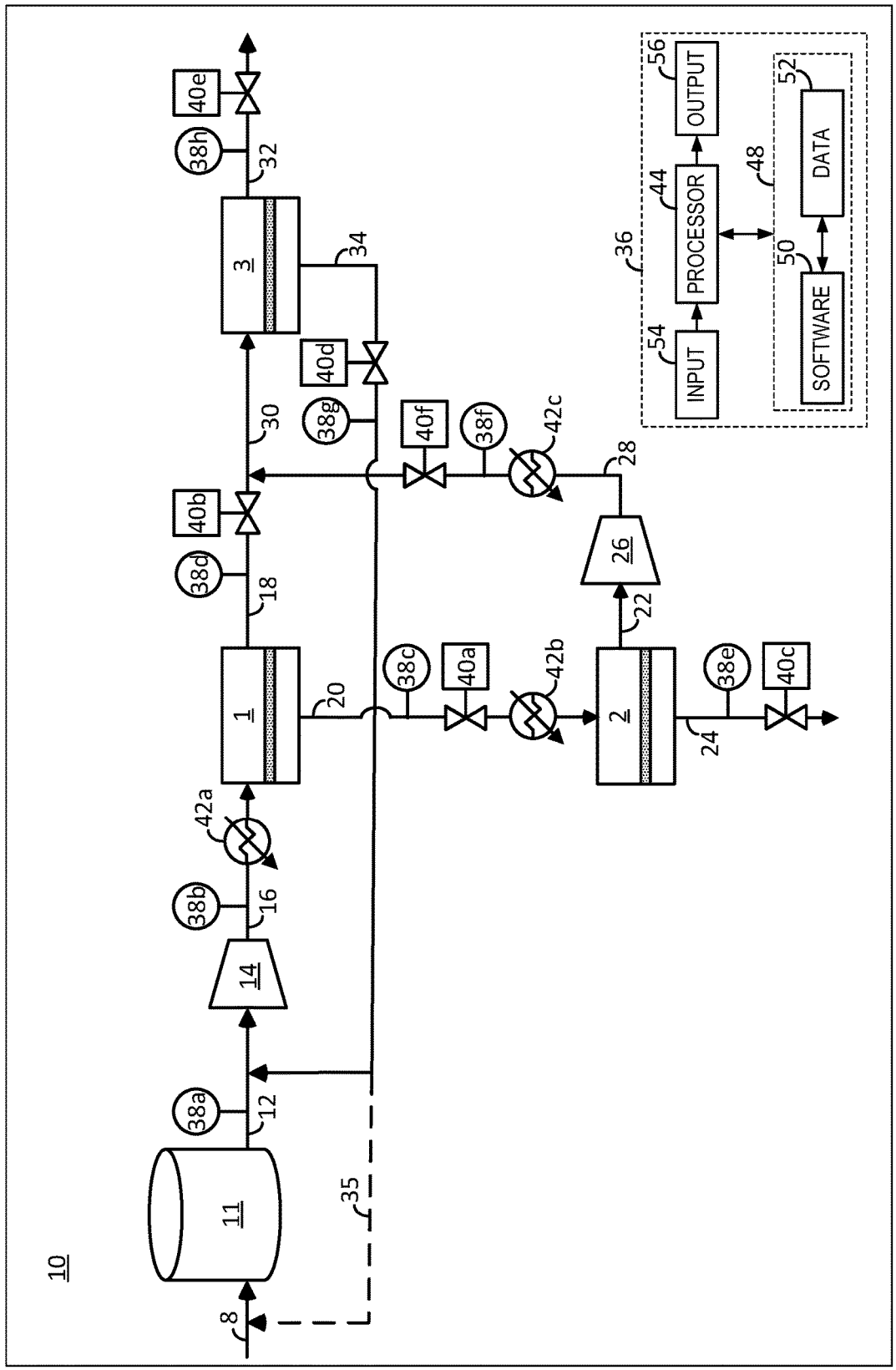
FIG. 2 is a block diagram of the example apparatus shown in FIG. 1 used in conjunction with a process control system in accordance with embodiments of the present disclosure.

FIG. 2 illustrates the apparatus 10 used in conjunction with an example process control system according to some embodiments of the present disclosure. The process control system may be configured to control the operation of the apparatus 10. For example, the process control system may assist in starting the process, stopping the process, and adjusting process parameters to change the process performance. In some embodiments, the control system may be designed to control the concentration of a desired component in the third retentate stream 32 or the second permeate stream 24, and/or to monitor and adjust system parameters to control energy consumption to reduce operational costs.

In some embodiments the control system may adjust or control a multitude of process parameters to maintain a product gas purity. For example, the product gas purity leaving the third retentate stream 32 may be controlled using the control system to be at least 80%, at least 85%, at least 90%, at least 91%, at least 92%, at least 93%, at least 94%, at least 95%, at least 96%, at least 97%, at least 98%, at least 99%, at least 99.5%, or at least 99.9%. In some embodiments, the product gas purity leaving the third retentate stream 32 may be controlled using the control system to be at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5%, or at least about 99.9%. In some non-limiting examples, the product gas in the third retentate stream 32 comprises methane.

In some embodiments, the process control system includes a controller 36, one or more process measuring devices (e.g., 38a-38h), one or more process control devices (e.g., the first gas transport device 14, the optional second gas transport device 26, one or more valves 40a-40e, and temperature control devices 42a-42c), and suitable connections that allows process information acquired by the one or more measuring devices to be transferred to the controller 36, and output information from the controller 36 to be transferred to the one or more process control devices to perform a process control action. Example process control actions may include using the process control devices to alter one or more of a pressure, flowrate, and/or temperature of a process stream based on one or more measured values from the process measuring devices.

Suitable connections may include transmitters that allow process signals, such as electrical signals or gas pressure signals (e.g., air, nitrogen, etc.), to be transmitted between the controller 36 and the measuring devices (e.g., 38a-38h) and the process control devices (e.g., 14, 26, 40a-40d, and 42a-42c). In some aspects, the electrical signals may be transferred via a wired connection or through a wireless network connection. Other hardware elements may be included in the process control system, for example, transducers, analog-to-digital (A/D) converters, and digital-to-analog (D/A) converters that allow process information to be recognizable in computer form, and computer commands accessible to the process. For visual clarity, the connections between the controller 36, the one or more measuring devices, and the one or more process control devices have been omitted from FIG. 2.

In some embodiments, the apparatus 10 includes one or more process measuring devices (e.g., 38a-38h). For example, the apparatus 10 may include one or more of an inlet gas line measuring device 38a provided in the inlet gas line 12, a feed gas line measuring device 38b configured in the gas feed line 16, a first permeate measuring device 38c configured in the first permeate stream 20, a first retentate measuring device 38d configured in the first retentate stream 18, a second permeate measuring device 38e configured in the second permeate stream 24, a second retentate measuring device 38f configured in the second retentate stream 28, a third permeate measuring device 38g configured in the third permeate stream 34, and a third retentate measuring device 38h configured in the third retentate stream 32. Each of the process measuring devices 38a-38h may be configured to measure a process parameter, or multiple process parameters, such as pressure, temperature, flow, composition, viscosity, humidity, moisture, or density.

In some embodiments, the one or more measuring devices 38a-38h includes a pressure measuring device. Suitable pressure measuring devices include, but are not limited to, pressure transducers, diaphragm bellows, Bourdon tubes, strain gauge, piezoelectric sensors, ionization gauges, and combinations thereof.

In some embodiments, the one or more measuring devices 38a-38h includes a flow measuring device. Suitable flow measuring devices include, but are not limited to, pitot tubes, orifice flow meters, turbine flow meters, electromagnetic field flow meters, neutron bombardment flow meters, ultrasound flow meters, hot-wire anemometry flow meters, and angular momentum flow meters, Coriolis mass flow meters, and combinations thereof.

In some embodiments, the one or more measuring devices 38a-38h includes a temperature measuring device. Suitable temperature measuring devices include, but are not limited to, thermocouples, thermistors (e.g., resistance sensor), oscillating quartz crystal thermometer, radiation pyrometers, and combinations thereof.

In some embodiments, the one or more measuring devices 38a-38h includes a density measuring device. Suitable density measuring devices include, but are not limited to, vibrating tube densometers, X-ray densometers, differential pressure densometers, and combinations thereof.

In some embodiments, the one or more measuring devices 38a-38h includes a viscosity measuring device. Suitable viscosity measuring devices include, but are not limited to, capillary viscometers, vibrating ball viscometers, and combinations thereof.

In some embodiments, the one or more measuring devices 38a-38h includes a humidity measuring device. Suitable humidity measuring devices include hygrometers that may be configured, for example, to measure precise dew point measurements.

In some embodiments, the one or more measuring devices 38a-38h includes a composition measuring device. Suitable composition measuring devices include, but are not limited to, potentiometry sensors, moisture content sensors (hygrometry or psychrometry), gas chromatography, refractive index device, ultrasound, spectroscopy system (e.g., UV, visible, IR, Mossbauer, Raman, atomic-emission device, X-ray device, electron, ion, nuclear magnetic resonance), polarography device, conductimetry device, mass spectrometry system, differential thermal analysis device, and thermogravi-metric analysis system, and combinations thereof.

Referring back to FIG. 2, the apparatus 10 includes one or more process control devices, such as valves (e.g., 40a-40e), temperature control devices (e.g., 42a-42c), the first gas transport device 14, and the second gas transport device 26. In some embodiments, a third gas transport device (not shown), such as a compressor or a blower, may be provided in the first permeate stream 20.

In some embodiments, the apparatus 10 includes one or more valves 40a-40f that is adjustable between a fully-open position and a fully-closed position, and is used to regulate the pressure of the process streams. For example, the apparatus 10 may include a first permeate valve 40a provided in the first permeate stream 20, a first retentate valve 40b, a second permeate valve 40c provided in the permeate stream 24, a third permeate valve 40d provided in the third permeate stream 34, a third retentate valve 40e provided in the third retentate stream 32, and a second retentate valve 40f provided in the continuing stream 28. Example valves for use in apparatus 10 include, without limitation, motor-driven valves, pneumatic values, and manually adjustable valves.

The apparatus 10 may include one or more temperature control devices (e.g., 42a-42c) that may be used to adjust the temperature (e.g., heat or cool) of the process streams. For example, the apparatus 10 may include one or more of a first stage temperature control device 42a configured in the gas feed line 16, a second stage temperature control device 42b configured in the first permeate stream 20, and a third stage temperature control device 42c configured in the second retentate stream 28. Alternatively, the third stage temperature control device 42c may be configured in the first retentate stream 18 or the mixed gas stream 30. Suitable temperature control devices 42a-42c include devices that heat or cool the process stream, such as heat exchangers or electric heaters.

The controller 36 includes a processor 44 and a memory 48 that includes software 50 and data 52, and is designed for storage and retrieval of processed information to be processed by the processor 44. The processor 44 includes an input 54 that is configured to receive process signals from the one or more of the measuring devices (38a-38h) and the one or more of the process control devices (e.g., 14, 26, 40a-40f, and 42a-42c) via the input 54. The controller 36 may operate autonomously or semi-autonomously, or may read executable software instructions from the memory 48 or a computer-readable medium (e.g., a hard drive, a CD-ROM, flash memory), or may receive instructions via the input 54 from a user, or another source logically connected to a computer or device, such as another networked computer or server. For example, the server may be used to control the apparatus 10 via the controller 36 on-site or remotely.

The processor 44 may process the process signals to generate an output 56, which may take the form of a process control action. Example process control actions may include sending signals to the one or more process control devices (e.g., 14, 26, 40a-40f, and 42a-42c) to effectuate a change in one or more process parameters (e.g., pressure, flowrate, and/or temperature) of one or more process streams in apparatus 10.

In some embodiments, the controller 36 includes programming to adjust the process parameters in the apparatus 10 using the one or more process control devices (e.g., 14, 26, 40a-40f, and 42a-42c) in response to measured values obtained from the one or more measuring devices (e.g., 38a-38h) to maintain a desired set-point in the third retentate stream 32, such as a desired pressure, a desired component composition, and/or a desired flowrate.

As a first example, the controller 36 may be programmed to monitor one or more process parameters in the third retentate stream 32 (e.g., methane content, pressure, etc.) using the third retentate measuring device 38h. Once a change in the process parameter is detected or a user-specified threshold has been reached, the pressure of the third retentate stream 32 may be adjusted using the third retentate valve 40e in order to maintain the desired set-point. Alternatively or additionally, the feed gas line measuring device 38b may be used to monitor one or more process parameters in the feed gas line 16, where the desired set-point in the third retentate stream 32 is maintained by steering the pressure in the third permeate stream 34 using the third permeate valve 40*d*.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired set-point in the second permeate stream 24, such as a desired pressure, a desired component composition, and/or a desired flowrate.

As a second example, the controller 36 may include software 50 that is programmed to acquire one or more process parameters in the second permeate stream 24 using the second permeate measuring device 38*e*. Once a change is detected or a user-specified threshold has been reached, the pressure of the second permeate stream 24 may be adjusted using the second permeate valve 40*c* to maintain the desired set-point.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired set-point in the first permeate stream 20, such as a desired pressure, a desired component composition, and/or a desired flowrate.

In a third example, the controller 36 is programmed to acquire one or more process parameters in the first permeate stream 20 using the first permeate measuring device 38*c*. Once a change is detected or a user-specified threshold has been reached, the pressure of the first permeate stream 20 may be adjusted using the first permeate valve 40*a* to maintain the desired set-point. In one non-limiting example, a gas component composition (e.g., methane) in the first permeate stream 20 is measured and controlled to maintain the desired set-point by adjusting the pressure in the first permeate stream 20 using the first permeate valve 40*a*.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired set-point in the third permeate stream 34, such as a desired pressure, a desired component composition, and/or a desired flowrate.

In a fourth example, the controller 36 is programmed to acquire one or more process parameters in the third permeate stream 34 using the third permeate measuring device 38*g*. Once a change is detected or a user-specified threshold has been reached, the pressure of the third permeate stream 34 may be adjusted using the third permeate valve 40*d* to obtain the desired set-point. In one non-limiting example, the pressure of the third permeate stream 34 is measured and controlled to be the same or substantially the same as the pressure of the inlet gas line 12, which may be measured using the inlet gas line measuring device 38*a*.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired set-point in the second retentate stream 22 and/or the continuing stream 28, such as a desired pressure, a desired component composition, and/or a desired flowrate.

In a fifth example, the controller 36 is programmed to acquire one or more process parameters in the second retentate stream 22 and/or the continuing stream 28 using the second retentate measuring device 38*f*. Once a change is detected or a user-specified threshold has been reached, the pressure of the continuing stream 28 may be adjusted using the second retentate valve 40*f* to maintain the desired set-point in the continuing stream 28. In one non-limiting example, the pressure of the continuing stream 28 is measured using the second retentate measuring device 38*f* and adjusted using the second retentate valve 40*f* such that the pressure of the continuing stream 28 is sufficient to be added to the first retentate stream 18. For example, the continuing stream 28 may be adjusted by the second retentate valve 40*f* to be the same or substantially the same as the pressure of the first retentate 18, which may be measured using the first retentate measuring device 38*d*.

Additionally, or alternatively, the controller 36 may be programmed to acquire one or more process parameter in the first retentate stream 18 using the first retentate measuring device 38*d*. Once a change is detected or a user-specified threshold has been reached, the pressure of the first retentate stream 18 may be adjusted using the first retentate valve 40*b*. In one non-limiting example, the pressure of the first retentate stream 18 is measured using the first retentate measuring device 38*d* and is adjusted using the first retentate valve 40*b* such that the pressure of the first retentate stream 18 is sufficient to be combined with the continuing stream 28.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired set-point in the inlet gas line 12 and/or the feed gas line 16, such as a desired pressure, a desired component composition, and/or a desired flowrate.

In some embodiments, the controller 36 includes programming to adjust process parameters in the apparatus 10 using the one or more process control devices (e.g., 14, 26, 40*a*-40*f*, and 42*a*-42*c*) in response to measured values obtained from the one or more measuring devices (e.g., 38*a*-38*h*) to maintain a desired temperature set-point for the first membrane separation stage 1, and/or the second membrane stage 2, and/or the third membrane separation stage 3.

In a sixth example, the controller 36 is programmed to acquire one or more process parameters in the apparatus 10 using one or more of the process measuring devices (e.g., 38*a*-38*h*) and adjust the temperature of operation temperature of the first membrane separation stage 1, and/or the second membrane separation stage 2, and/or the third membrane separation stage 3 using the first temperature control device, and/or the second stage temperature control device 42*b*, and/or the third stage temperature control device 42*c* to obtain a desired temperature set-point. The temperature of the first membrane separation stage 1, the second membrane stage 2, the third membrane separation stage 3 may be controlled to be the same or different.

Figure 3:
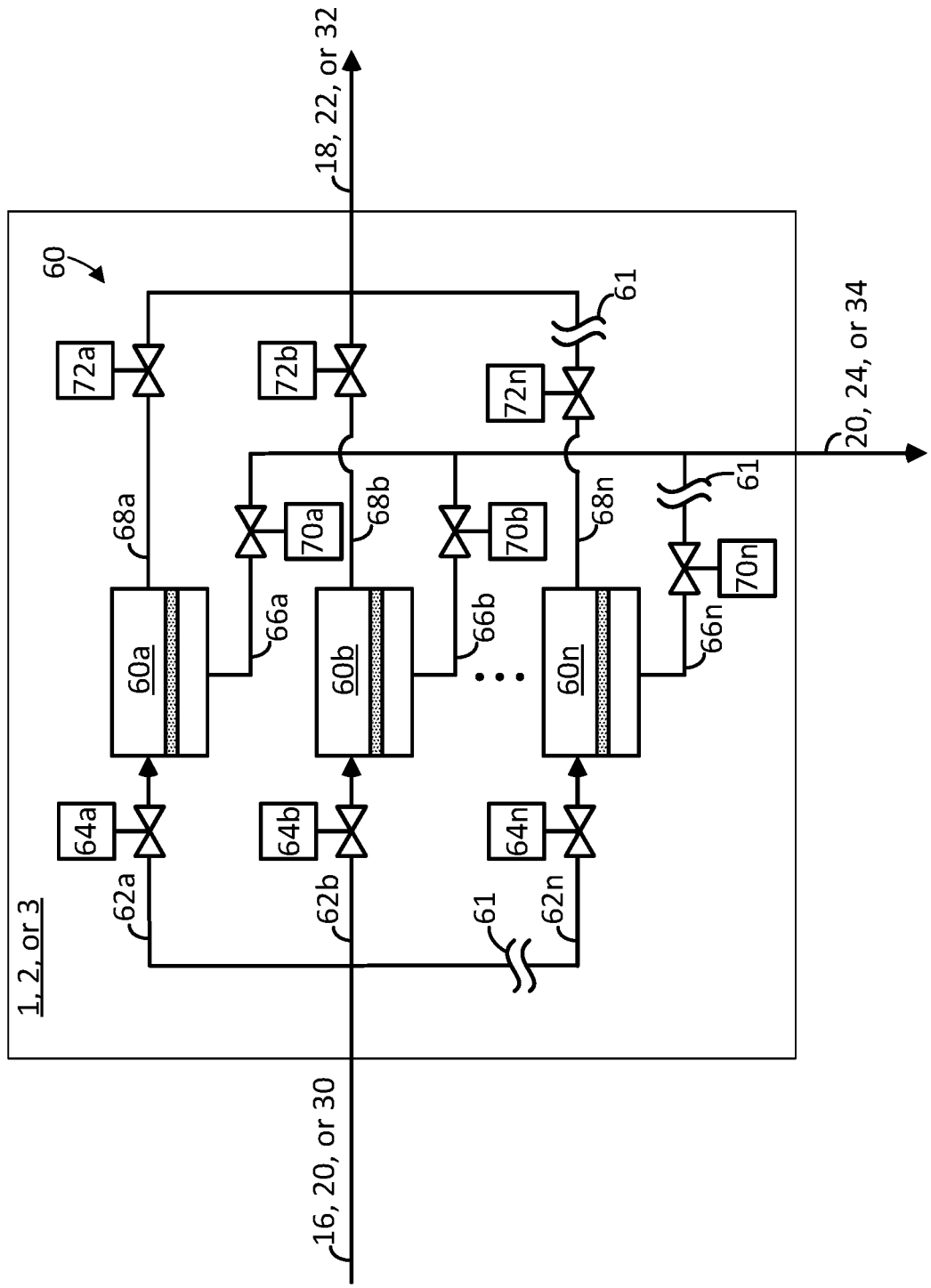
FIG. 3 is a block diagram of an example of a plurality of membranes configured within one or more of the first membrane stage, the second membrane stage, and/or the third membrane stage in accordance with embodiments of the present disclosure.

Referring now to FIG. 3, one or more of the membrane stages 1-3 in apparatus 10 may include a plurality of gas separation membranes 60 configured therein. The plurality of gas separation membranes 60 may be configured in parallel or in series.

In some embodiments, the one or more of the membrane stages 1-3 are configured with a first gas separation membrane unit 60*a*, a second gas separation membrane unit 60*b*, and (optionally, as indicated by break lines 61) one or more additional gas separation membrane units 60*n* in fluid communication with the incoming stream (e.g., 16, 20, or 30). The incoming stream is then split into multiple inlet streams to feed into the plurality of gas separation membranes 60. For example, the incoming stream may be split into a first interior membrane stage inlet stream 62a, a second interior membrane stage inlet stream 62b, and optionally one or more additional interior membrane stage inlet stream 62n. Each of the interior membrane stage inlet streams 62a, 62b, and 62n may be configured with a valve 64a, 64b, and 64n to regulate the flow rate to the respective gas separation membrane unit.

In some embodiments, each of the gas separation membrane units 60a, 60b, and 60n includes a gas separation membrane that separates the incoming gas mixture into interior membrane stage permeate streams 66a, 66b, 66n and retentate stream 68a, 68b, 68n, respectively. The permeate streams 66a, 66b, 66n may be combined to form a pooled permeate stream (e.g., 20, 24, and 34) that exits the one or more membrane stages 1-3. In some embodiments, permeate control valves 70a, 70b, 70n may be configured in the permeate streams 66a, 66b, 66n to regulate the gas flow rate to the pooled permeate stream. In an alternative arrangement, the permeate control valves 70a, 70b, 70n may be combined into a single valve positioned in the pooled permeate stream (e.g., 20, 24, 34). Similarly, each of the retentate streams 68a, 68b, 68n may be combined to form a pooled retentate stream (e.g., 18, 22, and 32) that exits the one or more membrane stages 1-3. Retentate control valves 72a, 72b, 72n may be configured to regulate the gas flow rate of the pooled retentate stream. In an alternative arrangement, the retentate control valves 72a, 72b, 72n may be combined into a single valve positioned in the pooled retentate stream (e.g., 18, 22, 32).

In some embodiments, the controller 36 is placed in electrical communication with the first interior control valve 64a, the second interior control valve 64b, the one or more additional interior control valve 64n, the permeate control valves 70a, 70b, 70n, and the retentate control valves 72a, 72b, 72n.

In some embodiments, the controller 36 includes programming to adjust the total surface area (e.g., increase or decrease) of the one or more membrane stages 1-3 using the one or more interior control devices (e.g., 64a, 64b, 64n, 70a, 70b, 70n, 72a, 72b, and 72n). The total surface area of the one or more membrane stages 1-3 may be adjusted manually by closing and opening the one or more interior control devices, for example, by a user. Alternatively or additionally, the total surface area of the one or more membrane stages 1-3 may be adjusted in response to measured values obtained from the one or more measuring devices (e.g., 38a-38h) to maintain a desired set-point in one or more of the process streams, such as a desired pressure, a desired component composition, and/or a desired flowrate. In some embodiments, the total surface area of the membrane stages 1-3 have a surface area ratio of 1:1:1, or about 1:1:1, or 1:2:1, or about 1:2:1, or from 1:1:1 to 1:4:1, or from about 1:1:1 to about 1:4:1. Tests have shown that adjusting the surface area ratio of the first membrane separation stage 1, the second membrane stage 2, and the third membrane separation stage 3 may enable, for example, the use of smaller or larger capacity compressors to be used in conjunction with apparatus 10, to adapt the apparatus 10 to specific needs.

As a seventh example, the controller 36 is programmed to acquire one or more process parameters in the apparatus 10 using the one or more of the process measuring devices (e.g., 38a-38h) and adjust the total surface area of the one or more membrane separation stages 1-3 by closing (e.g., to decrease surface area) or opening (e.g., to increase surface area) the valves to the first gas separation membrane unit 60a, the second gas separation membrane unit 60b, and/or the one or more additional gas separation membrane units 60n.

For example, if the flowrate of the gas mixture to apparatus 10 decreases, which may be measured using the inlet gas line measuring device 38a or the feed gas line measuring device 38b, it may be advantageous to reduce the total surface area of the one or more membrane stages 1-3 to maximize efficiency and to maintain a desired set-points during operation. This may be done, for example, by closing the one or more additional inlet cascade valve 64n, the one or more additional permeate valve 70n, and the one or more additional retentate valve 72n in response to the change in flowrate of the gas mixture to the apparatus 10.

Alternatively, if the flowrate of the gas mixture to the apparatus 10 increases, it may be advantageous to increase the total surface area of the one or more membrane stages 1-3. This may be done, for example, by opening the one or more additional inlet interior valve 64n, the one or more additional permeate valve 70n, and the one or more additional retentate valve 72n in response to the change in flowrate of the gas mixture to the apparatus 10.

Figure 4:
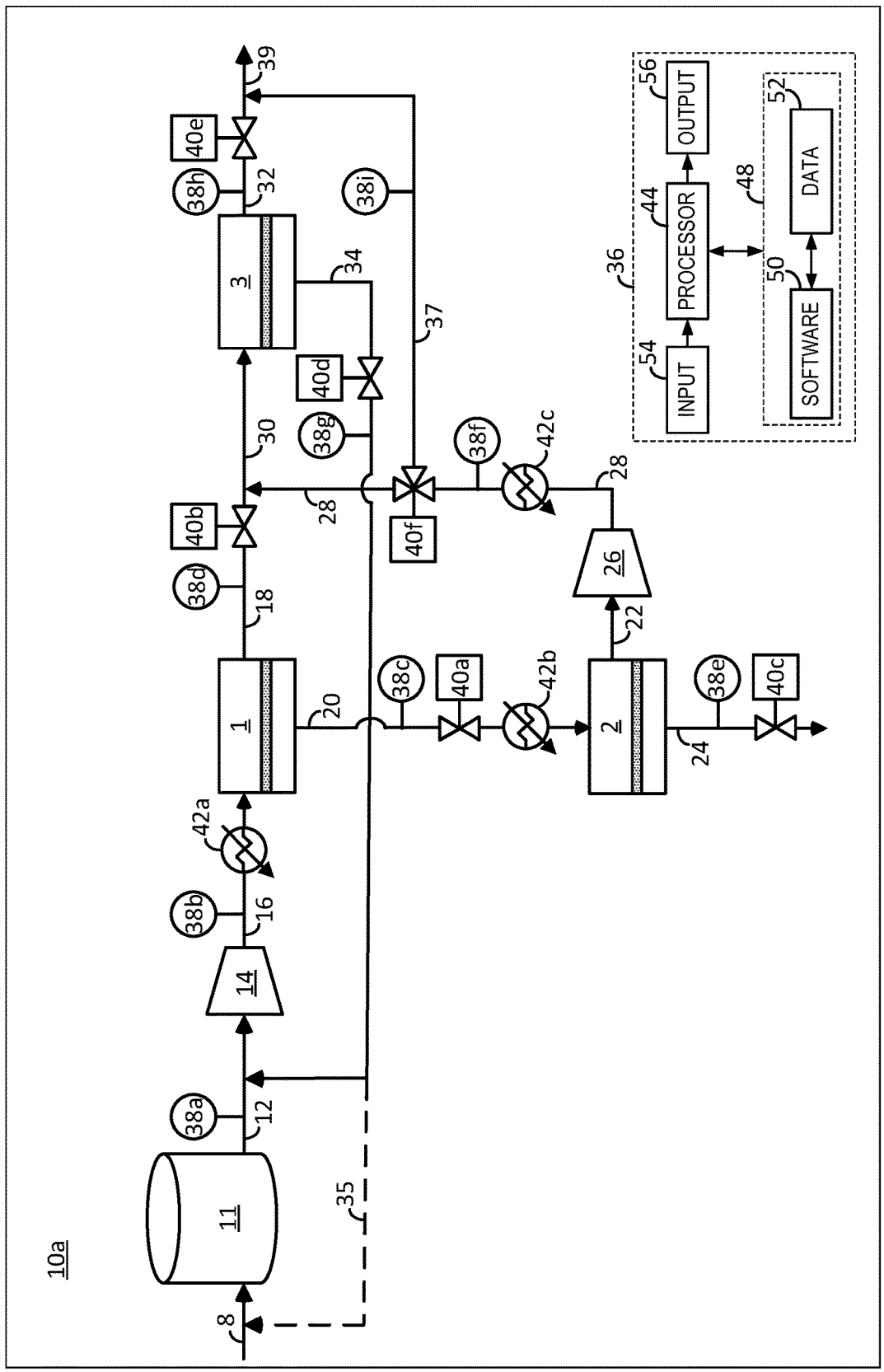
FIG. 4 is a block diagram of an alternative arrangement of the apparatus of FIG. 1 for separating a gas mixture in accordance with embodiments of the present disclosure.

FIG. 4 depicts an alternative arrangement of apparatus 10a according to some embodiments of the present disclosure. The apparatus 10a includes similar features as described with respect to FIGS. 1-3, and further includes a second continuing stream 37 that places the third retentate stream 32 in fluid communication with the continuing stream 28. During operation, the third retentate stream 32 is mixed with the second continuing stream 37 to form a mixed retentate stream 39. The mixed retentate stream 39 may be withdrawn as product, discarded, or further processed. In some embodiments, the optional second gas transport device 26 is removed from apparatus 10a. In some embodiments a measuring device (not pictured) and a valve (not pictured) are provided in the mixed retentate stream 39.

In some embodiments, the apparatus 10a further includes one or more process control devices, such as a valve 40f, that controls the pressure and gas flowrate of the continuing stream 28 and the second continuing stream 37. In some embodiments, the valve 40f may be adjusted between a fully-open position and a fully-closed position, which may be used to close the gas flow to the second continuing stream 37 and direct all the flow to the continuing stream 28, or vice versa. Alternatively, the valve 40f may be adjustable to divert a fraction of the gas to the second continuing stream 37 and the remaining fraction to the continuing stream 28. The valve 40f may be, for example, a motor-driven valve, a pneumatic valve, or a manually adjustable valve.

In some embodiments, the apparatus 10a includes one or more additional process measuring devices, such as a second continuing stream measuring device 38i. The second continuing stream measuring device 38i may be configured to measure a process parameter, or multiple process parameters, such as pressure, temperature, flow, composition, viscosity, humidity, moisture, or density. The second continuing stream measuring device 38i may include one or more of the process measuring devices described above.

In some embodiments, the controller 36 is configured to be in electrical communication with the valve 40f and the second continuing stream measuring device 38i. The controller 36 may include programming to adjust process parameters in apparatus 10a using the one or more process control devices (e.g., 14, 26, 40a-40f, and 42a-42c) in response to measured values obtained from the one or more process measuring devices (e.g., 38a-38i) to maintain a desired set-point in the one or more process stream in apparatus 10b, such as a desired pressure, a desired component composition, and/or a desired flowrate.

In an eighth example, the controller 36 may be programmed to acquire one or more process parameters in the second continuing stream 37 using the second continuing stream measuring device 38i. Once a change is detected or a user-specified threshold has been reached, the pressure or flow rate of the second continuing stream 37 and the continuing stream 28 may be adjusted using the valve 40f. In one non-limiting example, the pressure or flowrate of the second continuing stream 37 is measured using the second continuing stream measuring device 38i and adjusted such that the pressure of the second continuing stream 37 is sufficient to be added to the third retentate stream 32.

Figure 5:
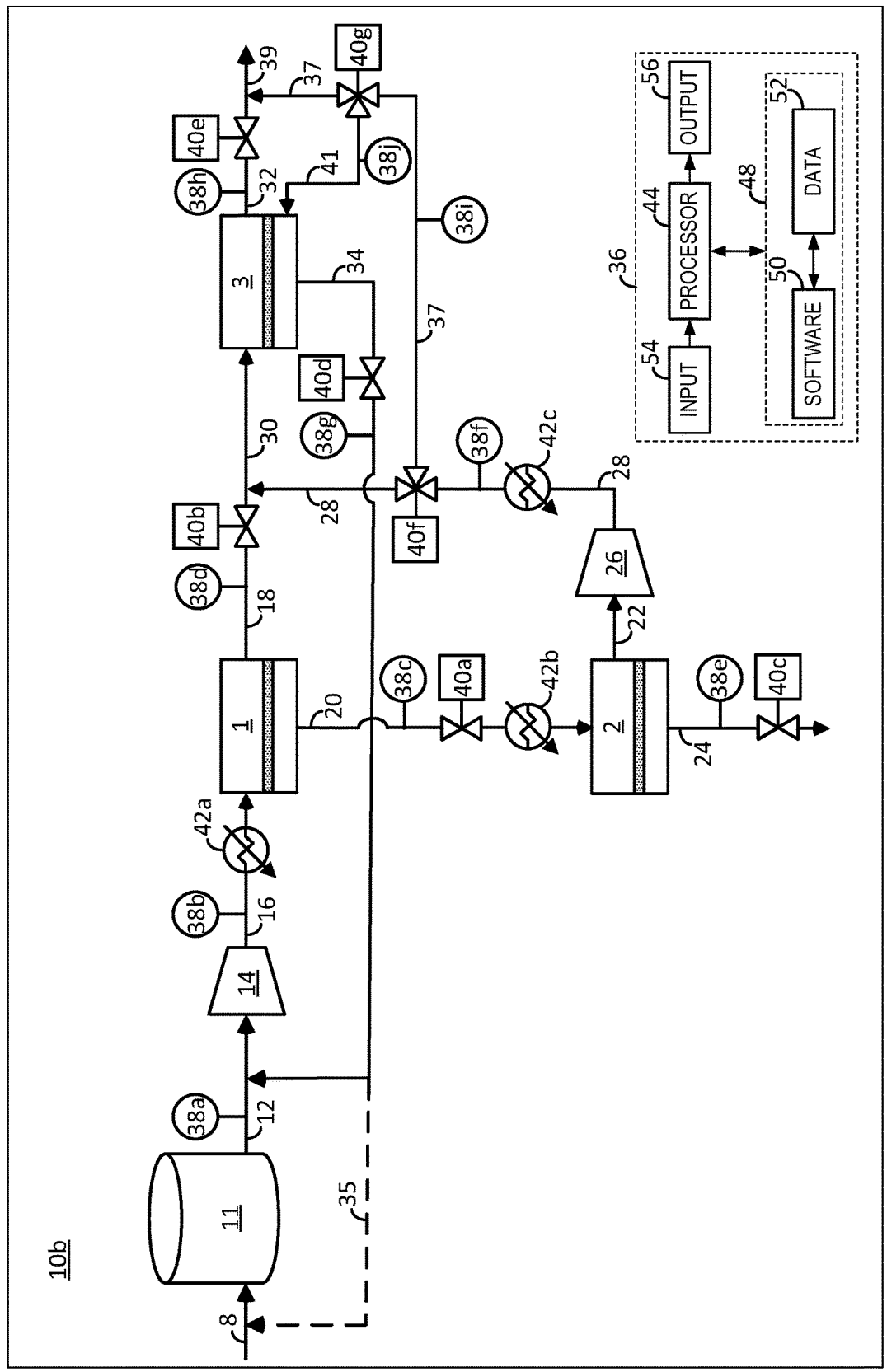
FIG. 5 is a block diagram of an alternative arrangement of the apparatus of FIG. 1 for separating a gas mixture in accordance with embodiments of the present disclosure.

FIG. 5 depicts an alternative arrangement of apparatus 10b according to some embodiments of the present disclosure. The apparatus 10b includes similar features as described with respect to FIGS. 1-4, and further includes a permeate sweep stream 41 that places the second continuing stream 37 in fluid communication with the permeate side of the third membrane separation stage 3. In some embodiments, the permeate sweep stream 41 is configured to enter the permeate side of the third membrane separation stage 3 such that the gas is swept across the membrane, and subsequently discharges into the third permeate stream 34. In some embodiments, the optional second gas transport device 26 is not present in apparatus 10b. In some embodiments a measuring device (not pictured) and a valve (not pictured) are provided in the mixed retentate stream 39.

In some embodiments, the apparatus 10b further includes one or more process control devices, such as a valve 40g, that controls the pressure and gas flowrate of the second continuing stream 37 and the permeate sweep stream 41. In some embodiments, the valve 40g may be adjusted between a fully-open position and a fully-closed position, which may be used to close the gas flow to the permeate sweep stream 41 and direct all the flow to the second continuing stream 37, or vice versa. Alternatively, the valve 40g may be adjustable to divert a fraction of the gas to the permeate sweep stream 41 and the remaining fraction to the second continuing stream 37. The valve 40g may be, for example, a motor-driven valve, a pneumatic valve, or a manually adjustable valve.

In some embodiments, the apparatus 10b includes one or more additional process measuring devices, such as a sweep flow measuring device 38j. The sweep flow stream measuring device 38 may be configured to measure a process parameter, or multiple process parameters, such as pressure, temperature, flow, composition, viscosity, humidity, moisture, or density. The sweep flow measuring device 38j may include one or more of the process measuring devices described above.

In some embodiments, the controller 36 is configured to be in electrical communication with the valve 40g and the sweep flow measuring device 38j. The controller 36 may include programming to adjust process parameters in apparatus 10b using the one or more process control devices (e.g., 14, 26, 40a-40g, and 42a-42c) in response to measured values obtained from the one or more process measuring devices (e.g., 38a-38j) to maintain a desired set-point in the one or more process stream in apparatus 10b, such as a desired pressure, a desired component composition, and/or a desired flowrate.

In a ninth example, the controller is programmed to acquire one or more process parameters in the permeate sweep stream 41 and the third retentate stream 32 using the sweep flow measuring device 38j and third retentate measuring device 38h, respectively. Once a change is detected or a user-specified threshold has been reached, in the third retentate measuring device 38h, the pressure or flow rate in the permeate sweep flow stream may be adjusted using the valve 40g to obtain a desired set-point in the third retentate stream 32.

EXAMPLES

The following examples set forth, in detail, ways in which the apparatus 10 separates a gas mixture, and will enable one of skill in the art to more readily understand the principles thereof. The following examples are presented by way of illustration and are not meant to be limiting in any way.

Example 1

Table 1 illustrates the Example 1 simulation data, which illustrates an example process of separating methane from biogas using apparatus 10, as depicted in FIGS. 1 and 2. For the simulation, the biogas from the gas source 11 was simulated having 68% carbon dioxide (w/w), 30.99% methane (w/w), 0.22% oxygen (w/w), and 0.79% nitrogen (w/w).

The results of the simulation are shown in Table 1:

TABLE 1

| | Drawing Reference Number | | | | |
|---|---|---|---|---|---|
| | 12 | 16 | 18 | 30 | 32 |
| Stream Name | Inlet Gas Line | Feed Gas Line | Stage 1 Ret | Stage3 Feed | Stage3 Ret |
| Temp (K) | 298.15 | 298.15 | 298.05 | 299.56 | 299.53 |
| Temp (° C.) | 25.0 | 25.0 | 24.9 | 26.41 | 26.38 |
| Pres (kPa) | 105 | 1130 | 1114 | 1114 | 1107 |
| Vapor mole fraction | 1.00 | 1.00 | 1.00 | 1.00 | 1.00 |
| Std vap 0 C m3/h | 1000.00 | 1409.09 | 817.74 | 970.31 | 561.22 |
| Flow rates in kg/h | | | | | |
| Methane | 393.67 | 470.22 | 429.88 | 468.08 | 391.53 |
| Carbon Dioxide | 863.96 | 1444.88 | 402.94 | 592.22 | 11.29 |
| Nitrogen | 10.00 | 13.90 | 11.79 | 13.69 | 9.78 |
| Component mass % | | | | | |
| Methane | 30.99 | 24.28 | 50.68 | 43.36 | 94.69 |
| Carbon Dioxide | 68.00 | 74.62 | 47.51 | 54.86 | 2.73 |
| Nitrogen | 0.79 | 0.72 | 1.39 | 1.27 | 2.37 |

As shown in Table 1, the third retentate stream 32 is significantly higher in methane gas purity (94.69%) compared to methane gas purity (30.99%) in the initial inlet gas line 12. The fact that the apparatus 10 is able to separate methane from biogas, to a purity of greater than 80%, and further greater than 94%, suggests that the apparatus 10 is suitable commercial gas separation, and, in particular, for commercial methane gas separation from biogas.

Example 2

Sample A. Sample A (S-A) is run using apparatus 10, as depicted in FIGS. 1 and 2. The first gas transport device 14 and the second gas transport device 26 are each compressors. In other words, the apparatus is equipped with two compressors.

Comparative Sample B. Comparative Sample B (CS-B) is run using Comparative Apparatus 3T. The Comparative Apparatus 3T is the same as the apparatus 10 depicted in FIGS. 1 and 2, except that the second retentate stream is immediately recycled back to the initial gas inlet via a recycle line, instead of forming a mixed gas stream that flows through the third membrane separation stage. Comparative Apparatus 3T utilizes a single compressor in the location of the first gas transport device 14 depicted in FIG. 1.

Comparative Sample C. Comparative Sample C (CS-C) is run using Comparative Apparatus 3TI. The Comparative Apparatus 3TI is the same as the apparatus Comparative Apparatus 3T descriptive above, except that a booster device is connected to the line carrying the first permeate stream from the first membrane separation stage to the second membrane separation stage. As in Comparative Apparatus 3T, the Comparative Apparatus 3TI second retentate stream is immediately recycled back to the initial gas inlet via a recycle line, instead of forming a mixed gas stream that flows through the third membrane separation stage.

The first membrane stage, the second membrane stage, and the third membrane stage of each of Sample A, Comparative Sample B, and Comparative Sample C are equipped with an "FH" membrane (commercially available as CO-xxxFH, from Ube Industries, Ltd., where "xxx" refers to the size of the membrane), as shown in Table 2.

The inlet gas line 12 of each of Sample A, Comparative Sample B, and Comparative Sample C is supplied with either (i) a "standard" (or "std") biogas feed that contains 55% $CH_4$, 44% $CO_2$, and 1% Air (20% $O_2$, 80% $N_2$); or (ii) a "high" biogas feed that contains 80% $CH_4$, 19% $CO_2$, 1% Air (20% $O_2$, 80% $N_2$), as shown in Table 2 (percentages based on volume). The biogas feed (i.e., the raw gas feed) flow is run between normal meter cubed per hour (1,000 $Nm^3$/hr) to 4,045 1,000 $Nm^3$/hr, as shown in Tables 2.

For each of Sample A, Comparative Sample B, and Comparative Sample C: (i) the biogas compressed to 11 bar(G) (1100 kPa); and (ii) gas is purged to free air with 0.5% methane loss overall. The results are shown in Table 2.

In Table 2, "RF" refers to the ratio per inlet raw gas. RF is calculated in accordance with the following Equation 1:

$$RF = \frac{\text{Gas Inlet First Compressor}\,(Nm3/hr)}{\text{Raw Biogas Feed}\,(Nm3/hr)}. \quad \text{Equation 1}$$

TABLE 2

Example 2 Samples Run with FH Membranes

| | Sample | | | | | | | | | | | | |
|---|---|---|---|---|---|---|---|---|---|---|---|---|---|
| | S-A1 | CS-C1 | S-A2 | CS-B1 | CS-C2 | S-A3 | CS-C3 | S-A4 | CS-C4 | CS-B2 | CS-B3 | CS-C5 | S-A5 |
| Apparatus Type | App. 10 | 3TI | App. 10 | 3T | 3TI | App. 10 | 3TI | App. 10 | 3TI | 3T | 3T | 3TI | App. 10 |
| Raw Gas Feed (Nm³/hr) | 1000 | 1000 | 1000 | 1000 | 1000 | 1035 | 1040 | 4000 | 4000 | 4000 | 4000 | 4020 | 4045 |
| Biogas Feed Type | std | std | std | std | std | std | std | high | high | high | high | high | high |
| Compressor 1 Nm³/hr | 1623 | 1626 | 1631 | 1743 | 1766 | 1675 | 1815 | 6086 | 5806 | 5836 | 6301 | 6354 | 6139 |
| Compressor 2 Nm³/hr | 109 | N/A | 111 | N/A | N/A | 101 | N/A | 269 | N/A | N/A | N/A | N/A | 265 |
| RF | 1.62 | 1.63 | 1.63 | 1.74 | 1.77 | 1.62 | 1.75 | 1.52 | 1.45 | 1.46 | 1.58 | 1.58 | 1.52 |
| Nm³/hr bio/membrane | 9.39 | 9.27 | 9.27 | 7.51 | 7.50 | 9.61 | 7.82 | 14.11 | 13.30 | 12.93 | 10.55 | 10.99 | 14.28 |
| Total Product (Nm³/hr)* | 563 | 563 | 563 | 563 | 562 | 583 | 586 | 3276 | 3278 | 3279 | 3278 | 3296 | 3315 |
| Recovery of CH₄* (vol %) | 99.50 | 99.51 | 99.50 | 99.51 | 99.50 | 99.50 | 99.51 | 99.50 | 99.50 | 99.50 | 99.49 | 99.50 | 99.50 |

*In final product, such as from the third retentate stream 32 in Sample A.
N/A = not applicable As shown in Table 2, Example 2's S-A4 and S-A5 each is run under similar conditions compared to CS-B2, CS-B3, CS-C4, and CS-C5, including the use of high biogas fed at a flow rate of between 4,000 $Nm^3$/hr and 4,045 $Nm^3$/hr, yet S-A4 and S-A5 exhibits a higher $Nm^3$/hr bio/membrane value relative to the comparative samples (CS-B2, CS-B3, CS-C4, and CS-C5).

As shown in Table 2, Example 2's S-A3 is run under similar conditions compared to CS-C1, including the use of standard biogas fed at a flow rate of between 1,000 $Nm^3$/hr and 1,035 $Nm^3$/hr, yet S-A2 exhibits a desirable combination of a lower RF value and a higher $Nm^3$/hr bio membrane value relative to the comparative sample (CS-C1).

A higher $Nm^3$/hr bio/membrane value is advantageous because it indicates that fewer individual membranes are needed to obtain the same amount of methane in the final product (i.e., in the third retentate stream). Fewer membranes being included in the apparatus results in reduced economic costs. A lower RF value is advantageous because it indicates that a smaller capacity compressor may be utilized in the apparatus, which reduces the economic cost of the apparatus, reduces the amount of energy required to operate the apparatus, and reduces the physical space of the apparatus. Additionally, a lower RF value indicates that a higher volume of raw biogas can flow through a compressor of the same size, relative to an apparatus operating at a higher RF value, which suggests that the apparatus can handle processing a higher total volume of gas. For example, a sample with an RF of 1.4 with a compressor capacity of 1,500 Nm$^3$/hr can handle 1,071 Nm3/h raw gas (calculated as 1500/1.4=1,071 Nm$^3$/h), while a sample with an RF of 1.6 can only handle 937.5 Nm$^3$/h raw gas.

The present disclosure has described one or more preferred embodiments, and it should be appreciated that many equivalents, alternatives, variations, and modifications, aside from those expressly stated, are possible and within the scope of the invention. For example, the structure, arrangement, and elements of the apparatus described herein include alternative design choices and serve the purpose of adapting the apparatus to specific needs, such as specific input compositions or pressures, or specific output purity or yield, for example.

We claim:

1. An apparatus for separating a gas mixture having at least two components, comprising:
   a plurality of membrane separation stages including a first membrane stage, a second membrane stage, and a third membrane stage;
   the first membrane stage designed to separate the gas mixture into a first retentate stream and a first permeate stream;
   the second membrane stage designed to separate the first permeate stream into a second retentate stream and a second permeate stream;
   the third membrane stage designed to separate the second retentate stream into a third retentate stream and a third permeate stream;
   a continuing stream that places the first retentate stream in fluid communication with the second retentate stream;
   a first gas transport device with a first inlet in fluid communication with the gas mixture and a first outlet in fluid communication with the first membrane stage;
   a second gas transport device with a second inlet in fluid communication with the first retentate stream and a second outlet in communication with the continuing stream; and
   a controller in communication with at least one measuring device and the first gas transport device;
   wherein the at least one measuring device is designed to measure at least one parameter of the gas mixture, the first permeate stream, the second retentate stream, or the third retentate stream, and wherein the controller adapts a behavior of the first gas transport device in response to a change of the at least one parameter of the gas mixture, the first permeate stream, the second retentate stream, or the third retentate stream as measured by the at least one measuring device,
   wherein the second gas transport device is in communication with the controller, and wherein the controller adapts the behavior of the second gas transport device in response to a measurement of the at least one parameter by the at least one measuring device.

2. The apparatus of claim 1, wherein the at least one measuring device measures at least one parameter associated with the third retentate stream.

3. The apparatus of claim 1, wherein the at least one measuring device is designed to measure at least one of a pressure, a temperature, a flow rate, a composition, a viscosity, a humidity, a moisture content, or a density of one of the first permeate stream, the second retentate stream, or the third retentate stream.

4. The apparatus of claim 1, wherein the controller is designed to adjust a process parameter of the apparatus in response to a measured value obtained from the at least one measuring device to maintain a desired set-point in the third retentate stream.

5. The apparatus of claim 4, wherein the desired set-point is selected from the group consisting of a desired pressure, a desired component composition, a desired flowrate, or combinations thereof.

6. The apparatus of claim 1, wherein the controller is designed to adjust a speed of rotation of the first gas transport device in response to a change in one of the at least one parameters of the gas mixture measured by the at least one measuring device.

7. An apparatus for separating a gas mixture having at least two components, comprising:
   a first membrane stage in fluid communication with a gas source comprising a reservoir of the gas mixture, wherein the first membrane stage separates the gas mixture into a first retentate stream and a first permeate stream;
   a second membrane stage in fluid communication with the first permeate stream, wherein the second membrane stage separates the first permeate stream into a second retentate stream and a second permeate stream;
   a continuing stream that places the second retentate stream in fluid communication with the first retentate stream to form a mixed retentate stream;
   a third membrane stage designed to separate the mixed retentate stream into a third permeate stream and a third retentate stream;
   a first gas transport device having an inlet in fluid communication with the second retentate and an outlet in fluid communication with the continuing stream;
   a controller in communication with at least one measuring device, the controller adapted to execute a stored program to adjust a speed of rotation of the first gas transport device to obtain a desired pressure set-point in the continuing stream; and
   wherein the speed of rotation of the first gas transport device is adjusted in response to a change in one or more process parameters measured by the at least one measuring device.

8. The apparatus of claim 7 further comprising a pretreatment unit positioned between the reservoir and the first membrane stage, the pretreatment unit designed to remove one or more contaminants from the gas mixture.

9. The apparatus of claim 7, wherein a measuring device of the at least one measuring device is in communication with the third retentate stream.

10. An apparatus for separating a gas mixture having at least two components, comprising:
    a first membrane stage in fluid communication with a gas source comprising a reservoir of the gas mixture, wherein the first membrane stage separates the gas mixture into a first retentate stream and a first permeate stream;

a second membrane stage in fluid communication with the first permeate stream, wherein the second membrane stage separates the first permeate stream into a second retentate stream and a second permeate stream;

a continuing stream that places the second retentate stream in fluid communication with the first retentate stream to form a mixed retentate stream;

a third membrane stage designed to separate the mixed retentate stream into a third permeate stream and a third retentate stream;

a first gas transport device having a first inlet in fluid communication with the second retentate stream and a first outlet in fluid communication with the continuing stream; and a controller programmed to acquire at least one process parameter associated with the second retentate stream or the continuing stream, and wherein the controller will adjust the first gas transport device to maintain a desired set-point in the continuing stream.

11. The apparatus of claim 10 further comprising a pretreatment unit in fluid communication with the reservoir and the first membrane stage, the pretreatment unit designed to remove one or more contaminants from the gas mixture.

12. The apparatus of claim 10 further including at least one measurement device in electrical communication with the controller.

13. The apparatus of claim 12, wherein a first measurement device of the at least one measurement device is in fluid communication with the third retentate stream.

14. The apparatus of claim 10 further including a second gas transport device, the second gas transport device including a second inlet in fluid communication with the reservoir and a second outlet in fluid communication with the first membrane stage.

15. The apparatus of claim 10, wherein the first membrane stage comprises a first plurality of membranes having a first total membrane surface area, the second membrane stage comprises a second plurality of membranes having a second total membrane surface area, and the second total membrane surface area is greater than the first total membrane surface area.

16. The apparatus of claim 15, wherein a first set of one or more interior control devices is coupled to the first membrane stage and a second set of one or more interior control devices is coupled to the second membrane stage, and the controller is designed to alter an operational status of at least one membrane of the first plurality of membranes or the second plurality of membranes via the first or second sets of the one or more interior control devices.

17. The apparatus of claim 1, wherein the first membrane stage comprises a first plurality of membranes having a first total membrane surface area, the second membrane stage comprises a second plurality of membranes having a second total membrane surface area, the third membrane stage comprises a third plurality of membranes having a third total membrane surface area, and the first total membrane surface area and the third total membrane surface area are about equal.

18. The apparatus of claim 7, wherein the first membrane stage has a first total membrane surface area, the second membrane stage has a second total membrane surface area, and the first total membrane surface area is smaller than the second total membrane surface area.

19. The apparatus of claim 7, wherein the gas mixture includes at least carbon dioxide and methane.

20. The apparatus of claim 7 further including one or more temperature control devices, wherein a first temperature control device of the one or more temperature control devices is in fluid communication with the first membrane stage.

* * * * *